United States Patent
Carson (10) Patent No.: US 11,839,669 B2
(45) Date of Patent: Dec. 12, 2023

(54) COSMETIC EMULSION BASES (CEB)

(71) Applicant: Suncoast Products LLC, Sarasota, FL (US)

(72) Inventor: John Clyde Carson, Sarasota, FL (US)

(73) Assignee: SUNCOAST PRODUCTS LLC, Sarasota, FL (US)

( * ) Notice: Subject to any disclaimer, the term of this patent is extended or adjusted under 35 U.S.C. 154(b) by 0 days.

(21) Appl. No.: 17/696,494

(22) Filed: Mar. 16, 2022

(65) Prior Publication Data

US 2023/0103526 A1  Apr. 6, 2023

Related U.S. Application Data (60) Provisional application No. 63/252,752, filed on Oct. 6, 2021.

(51) Int. Cl.

| | |
|---|---|
| *A61K 8/06* | (2006.01) |
| *A61K 8/31* | (2006.01) |
| *A61K 8/92* | (2006.01) |
| *A61Q 19/00* | (2006.01) |
| *A61K 8/37* | (2006.01) |
| *A61K 8/34* | (2006.01) |
| *A61K 8/02* | (2006.01) |

(52) U.S. Cl.
CPC ............ *A61K 8/062* (2013.01); *A61K 8/0254* (2013.01); *A61K 8/342* (2013.01); *A61K 8/375* (2013.01); *A61Q 19/00* (2013.01); *A61K 2800/10* (2013.01); *A61K 2800/48* (2013.01)

(58) Field of Classification Search
None
See application file for complete search history.

(56) References Cited

U.S. PATENT DOCUMENTS

| | | |
|---|---|---|
| 2,798,053 A | 7/1957 | Brown |
| 3,146,170 A | 8/1964 | Battista |
| 3,919,411 A | 11/1975 | Glass |
| 3,920,811 A | 11/1975 | Lund |
| 4,102,995 A | 7/1978 | Hebborn |
| 4,368,187 A | 1/1983 | Flom |
| 4,431,632 A | 2/1984 | Burns |
| 4,481,186 A | 11/1984 | Deckner |
| 4,514,385 A | 4/1985 | Damani |
| 4,514,386 A | 4/1985 | Yamahira |
| 4,566,977 A | 1/1986 | Hatfield |
| 4,738,842 A | 4/1988 | Dow |
| 4,956,170 A | 9/1990 | Lee |
| 5,296,166 A | 3/1994 | Leong |
| 6,365,656 B1 | 4/2002 | Green |
| 6,673,861 B2 | 1/2004 | Tabacchi |
| 6,831,107 B2 | 12/2004 | Dederen |
| 7,964,201 B2 | 6/2011 | Bertz |
| 9,540,473 B2 | 1/2017 | Rodrigues |
| 9,862,853 B2 | 1/2018 | Tamor |
| 9,963,534 B2 | 5/2018 | Rodrigues |
| 9,988,404 B2 | 6/2018 | Policello |
| 10,131,794 B2 | 11/2018 | Lu |
| 2005/0169874 A1 | 8/2005 | Zofchak et al. |
| 2011/0045037 A1 | 2/2011 | Tamarkin et al. |
| 2011/0250249 A1* | 10/2011 | Mateu ................ A61K 8/042 514/777 |
| 2014/0348759 A1* | 11/2014 | Hawkins ............ A61K 8/60 514/711 |
| 2018/0344618 A1* | 12/2018 | Motornov ........... A61K 8/8182 |

FOREIGN PATENT DOCUMENTS

WO  99/21532 A1  5/1999

OTHER PUBLICATIONS

Recent Dispersion Technology Using Liquid Crystal Chapter 12 Yuji Yamashita 2018 http://dx.doi.org/10.5772/intechopen.74156.
Liquid Crystal and α-gel-Based Emulsion and Soft Gel formulations Accounts of Materials & Surface Research Toshiyuki Suzuki Acc. Mater. Surf. Res. 2017, vol. 2 (No. 1), 21-40.
Formulation and Evaluation of Liquid Crystal Emulsion Containing Extra Virgin Olive Oil as Skin Anti-Aging International Journal of Applied Pharmaceutics vol. 12, Issue 4 2020.
Phase Behavior and Emulsion Stability of the AOT/Decane/WATER/NaCl System at Very Low Volume Fractions of Oil Yithanllili Bastidas, Lisset Hernandez, Issarly Rivas, Kareem Rahn-Chique and German Urbina-Villalba Revista del Centro de Estudios Interdisciplinarios de la Física vol. 3, 2014.
Emulsions—Part 2 a little (theory): emulsion stability Klaus Tauer MPI Colloids and Interfaces Am Mühlenberg, D-14476 Golm, Germany https://www.mpikg.mpg.de/886743/Emulsions_-1.pdf Created Nov. 16, 2005.
International Search Report in PCT/US22/45826 dated Jan. 24, 2023.
Written Opinion in PCT/US22/45826 dated Jan. 24, 2023.

* cited by examiner

*Primary Examiner* — Brian Gulledge
(74) *Attorney, Agent, or Firm* — Collard & Roe, P.C.

(57) ABSTRACT

At least one embodiment, relates to a method for making cosmetic emulsions comprising the steps of preparing a uniform (suspension) dispersion of at least one water soluble polymer in a mixture containing at least one fatty alcohol. The mixture is to be sufficiently uniform to be processed by flaking, pastillating, prilling or otherwise solidifying the mixture which is then to be added to a cosmetic emulsion oil phase before combining with a water phase.

13 Claims, 4 Drawing Sheets

FIG. 1

| Example 1 | |
|---|---|
| Ingredients | Wt% |
| Water Phase | |
| Distilled Water | 72.9 |
| Tetrasodium EDTA | 0.2 |
| Caprylyl Glycol | 0.6 |
| Phenoxyethanol | 0.6 |
| Triethanolamine (TEA) | 0.5 |
| Oil Phase | |
| Canola Oil (or Soybean Oil) | 10 |
| Glyceryl Tricaprate/caprylate | 10 |
| Mixed Tocopherols | 0.2 |
| Cosmetic Emulsion Base (CEB) | 5 |
| Total | 100 |

FIG. 2

| INGREDIENTS | Ex2 wt% | Ex3 wt% | Ex4 wt% | Ex5 wt% | Ex6 wt% | Ex7 wt% |
|---|---|---|---|---|---|---|
| Cetearyl Alcohol/ (Approximate HLB 0.5 to 1.0) | 40 | 40 | 50 | 50 | 50 | 55 |
| Glyceryl Monostearate (GMS (approximate HLB 3.4) | 20 | 20 | 26 | 28 | 27 | 27 |
| Stearic Acid TP (approx. HLB 1 – 2) (approx. HLB 18 with TEA) | 10 | 0 | 20 | 20 | 10 | 8 |
| Sodium Stearate (approx. HLB 18) | 0 | 0 | 0 | 0 | 10 | 7 |
| Behenic Acid/ (Approx HLB 1 - 2) (approx. HLB 18 with TEA) | 0 | 10 | 0 | 0 | 0 | 0 |
| Glyceryl Tricaprate/caprylate | 28 | 28 | 0 | 0 | 0 | 0 |
| C10-30 Alkyl Acrylates Cross polymer | 2 | 2 | 4 | 2 | 3 | 3 |
| TOTAL | 100 | 100 | 100 | 100 | 100 | 100 |

FIG. 3

| INGREDIENTS | Ex8 wt% | Ex9 wt% | Ex10 wt% | Ex11 wt% | Ex12 wt% | Ex13 wt% |
|---|---|---|---|---|---|---|
| Cetearyl Alcohol (approx. HLB 0.5 -1) | 40 | 50 | 50 | 45 | 50 | 50 |
| Glyceryl Monostearate (GMS) (approx. HLB 3.4) | 20 | 20 | 20 | 20 | 25 | 20 |
| Behentrimonium chloride (approx. HLB 15) | 10 | 20 | 20 | 25 | 7.5 | 25 |
| | 0 | 0 | 0 | 0 | 0 | 0 |
| Distearyldimonium chloride (approx. HLB 15) | 0 | 0 | 0 | 0 | 7.5 | 0 |
| Glyceryl Tricaprate/caprylate | 25 | 0 | 0 | 0 | 0 | |
| Guarhydroxypropyltrimonium Chloride | 0 | 0 | 10 | 5 | 5 | 0 |
| Chitosan Citrate | 0 | 0 | 0 | 0 | 0 | 5 |
| Polyquaternium 37 | 5 | 10 | 0 | 5 | 5 | 0 |
| TOTAL | 100 | 100 | 100 | 100 | 100 | 100 |

FIG. 4

| INGREDIENTS | Ex14 wt% | Ex15 Wt% | Ex16 wt% | Ex17 wt% | Ex18 wt% |
|---|---|---|---|---|---|
| Cetearyl Alcohol (approx. HLB 0.5 -1) | 40 | 40 | 50 | 50 | 50 |
| Glyceryl Monostearate (GMS) (approx. HLB 3.4) | 20 | 23 | 20 | 20 | 25 |
| Cetearyl Glucoside (and) Sorbitan Olivate | 10 | 0 | 0 | 0 | 0 |
| Polysorbate 60 (approx. HLB 15) | 0 | 10 | 20 | 0 | 0 |
| Polyglyceryl 10 Stearate (approx HLB12) | 0 | 0 | 0 | 20 | 15 |
| Glyceryl Tricaprate/caprylate | 25 | 20 | 0 | 0 | 0 |
| Xanthan Gum | 5 | 7 | 10 | 10 | 10 |
| TOTAL | 100 | 100 | 100 | 100 | 100 |

COSMETIC EMULSION BASES (CEB)

CROSS REFERENCE TO RELATED APPLCIATIONS

This application is a non-provisional application that hereby claims priority to U.S. Provisional Application Ser. No. 63/252,752 filed on Oct. 6, 2021, the disclosure of which is hereby incorporated herein by reference in its entirety.

BACKGROUND

There are two basic types of cosmetic emulsions: water-in-oil (w/o) and oil-in-water (o/w). At least one embodiment of the present invention is directed towards oil-in-water (o/w) emulsions. These consist of four major components. The two most important components are, of course, oil and water. Oils can be selected from a wide variety of diverse ingredients such as, but not limited to: fatty triglycerides, jojoba oil, mineral and petroleum oils, silicones, fluoro-compounds, cosmetic esters, fragrance compounds, oil soluble extracts and other ingredients whose major characteristic (from a cosmetic emulsions point-of-view) is that they are not miscible with water. The water phase contains, of course, water and may also contain other water-soluble ingredients such as: salts, lower alcohols, ethers, glycols, glycerol, polyglycerols, sugars, water soluble extracts, proteins, antimicrobials, preservatives, colorants and other ingredients that are miscible with water and have a use in cosmetic emulsions. As we know from experience, water and oil can be mixed mechanically to produce an emulsion. One of the most common examples of such an emulsion is a salad dressing made from olive oil and balsamic vinegar that is mixed by shaking, but, in time, it will separate into the two layers. It is to improve the stability and keep the oil and water together that the other two emulsion components are added. The first component is, usually, a combination of high and low HLB surfactants with, as examples (but not limited to), a Polysorbate, a soap or a fatty quaternary surfactant serving as the high HLB component and a fatty alcohol, a one or two mole fatty alcohol (or fatty acid) ethoxylate, or fatty polyol ester (such as glyceryl monostearate or a fatty sorbitan ester) being the low HLB surfactant. A high HLB is a HLB number greater than 10, a low HLB is a HLB number lower than 10.

It is noted that the HLB (Hydrophilic/Lipophilic Balance) system provides a means to compare surfactants by determining the relative weight of their water-soluble portion (hydrophilic) to their oil soluble portion (lipophilic). See Surfactants: Strategic Personal Care Ingredients, Anthony O'Lenick, Jr., Allured Publishing Corporation, 2014, ISBN 978-1-932633-96-2, Supplemental Chapter 4, pg. 81, pg. 124, the disclosure of which is hereby incorporated herein by reference in its entirety.

The high HLB surfactants, along with agitation, "break up" the oil into individual droplets and disperse the droplets throughout the water phase. The high HLB surfactants also help to define the droplet's size and we know from Stoke's Equation (and experience) that a smaller droplet size produces a more stable emulsion. NB.

In addition, the combination of high and low HLB surfactants can produce surfactant hydrate structures (i.e., liquid crystals and gel phase) in the water phase. The surfactant hydrate structures act as a barrier to the close approach and flocculation of the oil droplets, thus stabilizing the emulsion.

The final emulsion component is a water-soluble polymer that increases the viscosity of the water phase and is most often chosen to give a plastic flow rheology. Increasing the viscosity makes it more difficult for individual oil droplets to move in the water phase, thereby reducing their close approach and flocculation and further improving stability. Water soluble polymers such as (but not limited to), Carbomers, Pemulens™, Guar Gum (and derivatives), Xanthan Gum, Chitosan, Hydroxyethyl Celluloses and derivatives and acrylate polymers all find use as emulsion stabilizers.

SUMMARY

At least one embodiment, relates to a method for making cosmetic emulsions comprising the steps of preparing a uniform (suspension) dispersion of at least one water soluble polymer in a mixture containing at least one fatty alcohol. The mixture is to be sufficiently uniform to be processed by flaking, pastillating, prilling or otherwise solidifying the mixture which is then to be added to a cosmetic emulsion oil phase before combining with a water phase.

In at least one embodiment, the method further comprises the step of combining the fatty alcohol mixture with a low HLB surfactant and a high HLB surfactant to form a component that is then further processed by flaking, pastillating, prilling or otherwise solidifying the mixture which is then to be added to a cosmetic emulsion oil phase before combining with a water phase.

In addition, in at least one embodiment there is also a method for making cosmetic emulsions comprising the steps of providing at least one fatty alcohol; then providing at least one low HLB surfactant; and then providing at least one high HLB surfactant; and then mixing at least one fatty alcohol with at least one low HLB surfactant and at least one high HLB surfactant together to form a substantially uniformly dispersed mixture. The process also includes adding at least one water soluble polymer to the uniformly dispersed mixture to form an emulsifier blend. The process can then also include adding the emulsifier blend to a cosmetic emulsion oil phase; and then adding the oil phase to the water phase.

There is also a method for making cosmetic emulsions comprising the steps of: providing at least one fatty alcohol; providing at least one low HLB surfactant; providing at least one high HLB surfactant; mixing at least one fatty alcohol with the at least one low HLB surfactant and the at least one high HLB surfactant together to form a substantially uniformly dispersed mixture; and then adding at least one water soluble polymer to the uniformly dispersed mixture to form an emulsifier blend. The process also includes the step of adding the emulsifier blend to a cosmetic emulsion water phase; and then adding the water phase to the oil phase.

With the above method the cosmetic emulsions are made at higher temperatures—usually between 60° and 80° C. The high and low HLB surfactants are combined with the other oil phase ingredients and heated to 60° C. to 80° C. HLB is a balance between Hydrophilic and Lipophilic molecule of an amphiphilic Molecule (a molecule which is both). HLB is a number system that lets you know how oils and surfactants will likely interact. Surfactants have an HLB value—the higher the number the more hydrophilic (water soluble), the lower the number the more lipophilic (oil soluble). Oils and applications have an HLB requirement. Matching the HLB value with the HLB requirement will provide beneficial performance. Thus, the HLB number of the surfactants is selected to help provide the best emulsion.

The heating of this mixture is done to melt all of the oil phase ingredients and to mix them to make a uniform phase (sometimes the oil phase will need to be heated over 80° C. because of higher melting ingredients). When dispersed into the water phase (also heated to 60° C. to 80° C.), the high and low HLB surfactants migrate from the oil phase droplets into the water phase to form the surfactant hydrate structures. In addition, the high HLB surfactant will help to define the oil droplet size and will help to make the surface of the oil droplets more compatible with water, effects that help the formation of the emulsion and improve emulsion stability.

In common practice, the polymer is added to the water phase (or simply the water alone) as a first step, before heating, in order to disperse it. Adding a polymer to water can be problematic because it can form lumps as the polymer particles wet out and these lumps can be very difficult to break up. Also, the polymer may not disperse evenly— sticking to mixer blades and vessel walls and it can burn or char on contact with high temperature heating elements. It is to minimize these problems that conventional wisdom teaches us to make the polymer solution in the water phase as a first step when making a cosmetic emulsion.

Once the polymer is added to the water phase and it is uniform, then the emulsion is made by adding any remaining desired water phase ingredients, heating it to about 60° C. to 80° C. and adding the heated oil phase (containing the high and low HLB surfactants and also at about 60° C. to 80° C.) to the water phase. The emulsion is mixed well at temperature (until it is uniform) and then cooled, with continued mixing, to the desired drop temperature.

It has been found that the polymer can be added to the oil phase along with the high and low HLB surfactants and the other oil phase ingredients (U.S. Pat. No. 5,296,166). The oil phase is weighed out as in normal practice and then heated to melt any solid waxy ingredients and to bring it to the desired emulsification temperature. Before the oil and water phases are combined, the polymer is added to the oil phase and dispersed with mixing until a uniform suspension results. When the oil and water phases are then combined, the polymer is released from the oil phase and swells and solvates in the water phase producing the expected viscosity resulting in an emulsion with attributes comparable to a conventionally prepared emulsion. Importantly, the ratio of emulsifiers to water soluble polymer is limited to no greater than 0.5 to 1 in U.S. Pat. No. 5,296,166 the disclosure of which is hereby incorporated herein by reference. Thus, the resulting emulsion is a "gel" type relying upon the polymer to provide viscosity and stability.

Surprisingly, it has been found that an even more preferred method for adding the polymer to the oil phase and the method of the present invention, is to initially disperse the polymer in a blend of the high and low HLB surfactants and fatty alcohols. This allows for a more uniform dispersion of the polymer in the oil phase because it is already dispersed in the emulsifiers. Further, a much greater ratio of emulsifiers to water soluble polymer can be achieved allowing the creation of surfactant hydrate structures in the water phase to help stabilize the emulsion, provide enhanced slip and feel and add structure to the emulsion. Thus, the ratios of emulsifier to water soluble polymer in the present invention is more typically in the range of about 9 to 1 to over 30 to 1 providing an effective amount of polymer and sufficient emulsifier to form liquid crystals and gel phase.

The advantages of creating a dispersion of the water soluble polymer in the emulsifiers are: 1) producing a single component to be weighed and added to the rest of the oil phase, thus reducing costs and time needed for formulating and manufacturing cosmetic emulsions, 2) having the combination of the high and low HLB surfactants and added polymer prepared as a flake, pastille, prill or other solid product form that allows for easier handling, weighing and storage, 3) allowing the addition of the polymer to the emulsifiers at a controlled temperature to avoid burning or degradation (even if the high and low HLB surfactants may have to be heated to a high temperature to melt and mix them, they can be cooled to a lower temperature before the polymer is added), 4) providing a complete emulsifying and emulsion stabilization system needing no other emulsifying ingredients, unless desired for feel or aesthetic reasons 5) reducing the inventory and quality control requirements because fewer ingredients have to be warehoused and 6) most importantly, ensuring the uniform dispersion of the polymer in the oil phase by pre-dispersing it uniformly in the fatty alcohols and high and low HLB surfactants.

It is most surprising that the polymer is released so quickly from the oil phase becoming an effective viscosity builder in the water phase almost immediately upon the combination of the two phases.

Not all combinations of high and low HLB surfactants are compatible nor are they necessarily compatible with the stabilizing polymer. This is the case for the combination of the high and low HLB surfactants with the polymer itself, for the combination when mixed with oils in the oil phase and for the final emulsion made by combining the oil and water phases. Thus, combinations of high and low HLB surfactants with specific polymers are detailed in the present invention that produce stable mixtures in and of themselves, and stable mixtures with the oil phase and ultimately produce stable oil-in-water emulsions.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION

A test emulsion formula was developed to allow comparison of the stability and physical parameters of the various emulsion bases. The test emulsion formula for a cosmetic lotion is given in Example 1 shown in FIG. 1.

Figure 1:
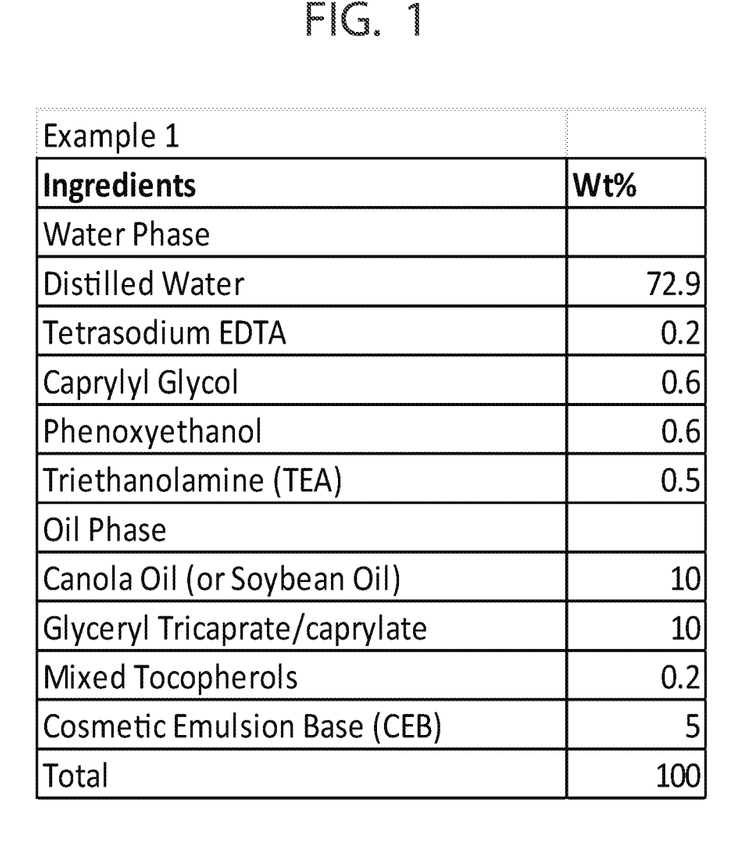
FIG. 1 is a listing of ingredients in wt % for a first example.

The Test Lotion Formula (Example 1) is prepared by weighing and combining the Water and Oil phases separately. Both phases are mixed separately and heated to about 65 to 75° C. Triethanolamine (TEA) (or another base of choice) is needed to neutralize the fatty acid (if used—as in the anionic emulsion bases) and the C10-30 Alkyl Acrylates Cross polymer. TEA is not needed for the nonionic or cationic emulsion bases and can be replaced by water. Once both phases are mixed until uniform and at temperature, they are combined by adding the water to the oil phase with mixing. Mixing is continued with the temperature at about 65 to 75° C. for about ½ hour. The Test Lotion is then cooled to the desired drop temperature with mixing.

Alternatively, the oil phase can be added to the water phase with mixing with both phases at about 65 to 75° C. Mixing is continued for about ½ hour at about 65 to 75° C. and then the Test Lotion is cooled to the desired drop temperature with mixing. In at least one embodiment and as an option to at least one, more than one or all of the examples the water phase can be added as at least a 50% heated water phase. As an option the remaining step of adding water can be in the form of adding cold water for the remaining balance of water.

As written, the Test Lotion contains 5% Cosmetic Emulsion Base (CEB). This is for purposes of comparing the various CEBs. In practice, the amount can be adjusted to suit the aesthetics and particular needs of the emulsion formulator. For example, if the amount is increased, a thick lotion or a cream instead of a lotion can be produced.

The Test Lotions were evaluated for pH, viscosity and tested for stability at RT, 50° C. and Freeze/Thaw. Photomicrographs of the emulsions were taken.

The following examples are provided as illustrations of acceptable and unacceptable emulsion stabilizer systems, but they are not intended to provide a complete listing of all acceptable or unacceptable combinations. The Test Emulsion Formula, as provided in Example 1, is used to make finished emulsions with each of the following examples thus, the Examples can be compared for pH, viscosity, stability, particle size and distribution and aesthetic properties.

Experimental Results

Figure 2:
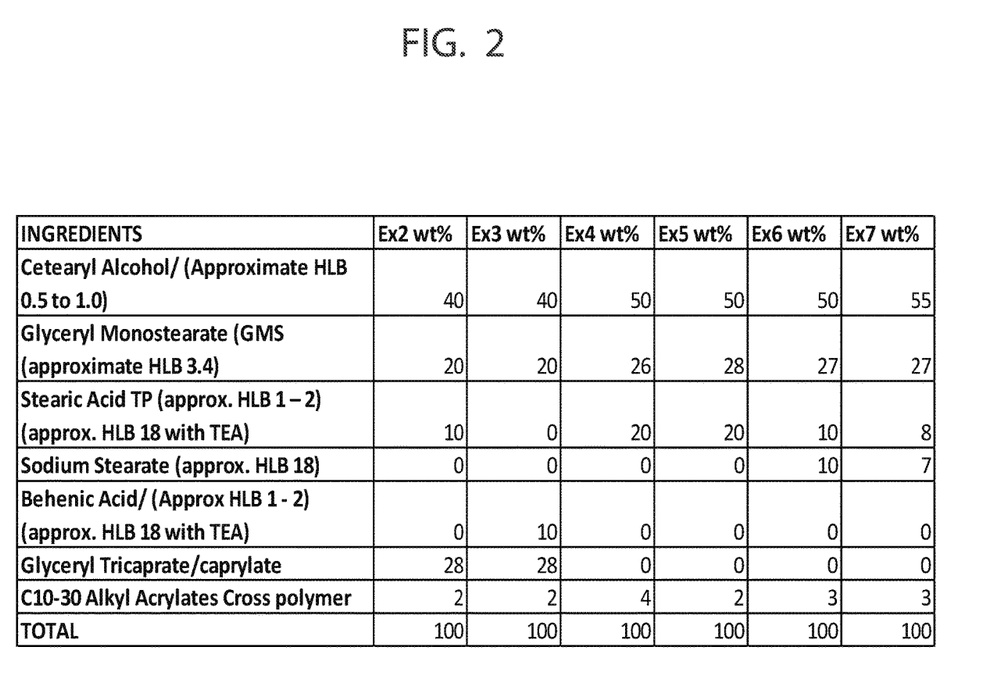
FIG. 2 is a listing of ingredients in wt % for examples 2-7.

There are six examples shown in shown in FIG. 2 which include examples 2-7 which are for anionic cosmetic emulsion bases.

These examples illustrate the concept of combining the high and low HLB surfactants and a stabilizing polymer to form a single composition using anionic high HLB surfactants. Anionic Emulsion Bases can be made with anionic and/or nonionic water soluble polymers. Cationic water soluble polymers will be incompatible.

The Examples 2, 3 and 6 were made by combining the first four ingredients. These components are heated, with mixing, to about 80 to 85° C., ensuring that all components are melted, then cooling with mixing to 65 to 75° C. The polymer (C10-30 Alkyl Acrylates Cross polymer) is added with mixing and mixed until it is visibly uniform, keeping the temperature at 65 to 75° C. When the mixture was uniform, it was poured onto aluminum foil, allowed to cool to room temperature, removed from the aluminum foil and broken into suitably sized pieces. Examples 4 and 5 were made by combining the first three ingredients, heating, with mixing, to about 80 to 85° C., ensuring that all components were melted, then cooling with mixing to 65 to 75° C. The polymer was added with mixing and mixed until the mixture was uniform. When the mixture was uniform, it was poured onto aluminum foil, allowed to cool to room temperature, removed from the aluminum foil and broken into suitably sized pieces. It was determined that the addition of Glyceryl Tricaprate/caprylate (used in Examples 2 and 3) produced a flake that was too soft and would present difficulties upon storage and shipping. Examples 4, 5 and 6 remedied that, but Example 4 produced an undesirable "rubbery" texture in the Test Lotion (Example 1) upon ageing, while Examples 5 and 6 do not. Example 5 makes a high viscosity lotion (light cream) with acceptable stability. Example 6 allows the Test Lotion (Example 1) to be made without the use of Triethanolamine to neutralize the stearic acid because sufficient base is provided by the sodium stearate to neutralize both the stearic acid and the C10-30 Alkyl Acrylates Cross polymer. If only sodium stearate is used (instead of a combination of stearic acid and sodium stearate, as in Example 6), it reacts with the C10-30 Alkyl Acrylates Cross polymer causing it to precipitate and clump up in the Cosmetic Emulsion Base formula. The Example 7 was made by combining the first four ingredients. These components are heated, with mixing, to about 80 to 85° C., ensuring that all components are melted, then cooling with mixing to 65 to 75° C. The polymer (C10-30 Alkyl Acrylates Cross polymer) is then added with mixing and mixed until it is visibly uniform, keeping the temperature at 65 to 75° C. When the mixture is uniform, it is poured onto aluminum foil, allowed to cool to room temperature, removed from the aluminum foil and broken into suitably sized pieces.

Example 7 also allows the Test Lotion (Example 1) to be made without the use of Triethanolamine to neutralize the stearic acid because sufficient base is provided by the sodium stearate to neutralize both the stearic acid and the C10-30 Alkyl Acrylates Cross polymer. The Example 7 lotion is stable for 2 months @50° C. and for at least 6 months at Room Temperature.

Figure 3:
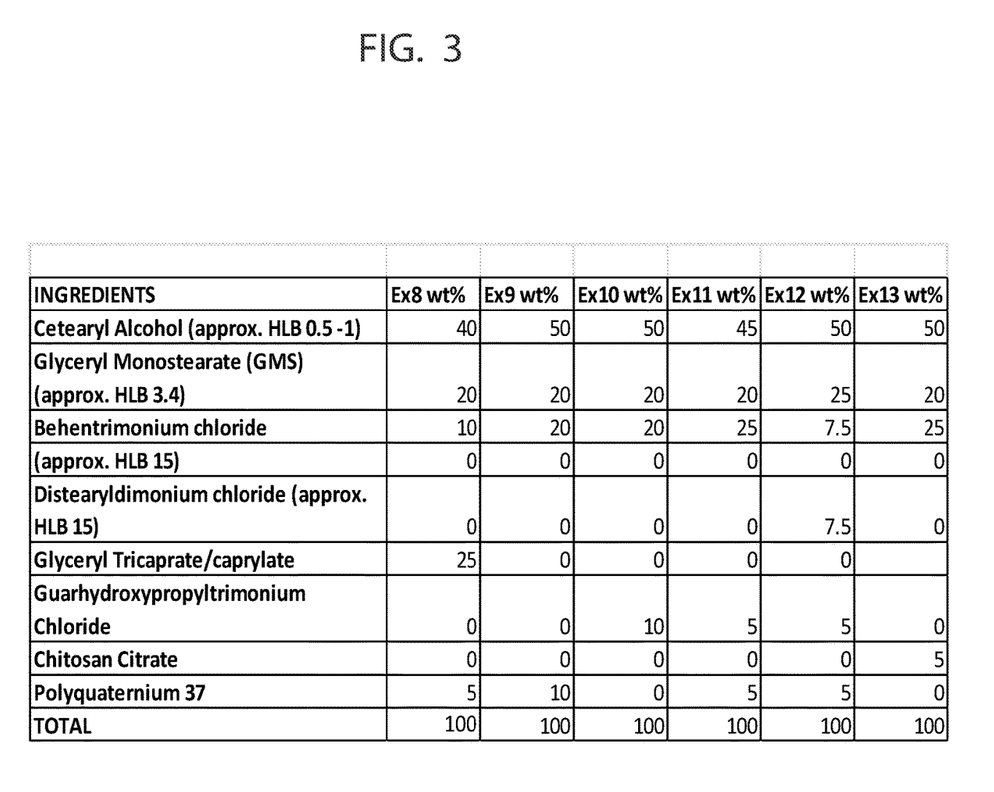
FIG. 3 is a listing of ingredients in wt % for examples 8-13.

FIG. 3 shows the ingredients in wt % for examples 8-13 which are examples of cationic emulsion bases.

With these examples, the Test Emulsions were evaluated for pH, viscosity and tested for stability at RT, 50° C. and Freeze/Thaw. Photomicrographs of the emulsions were taken.

These examples illustrate the concept of combining the high and low HLB surfactants and a stabilizing polymer to form a single composition using cationic high HLB surfactants. Cationic Emulsion Bases can be made with cationic and /or nonionic water soluble polymers. Anionic water soluble polymers will be incompatible Example 8 was made by combining the first four ingredients then heating with mixing to melt and solubilize them. Once uniform, the mixture was cooled to 65 to 75° C. and the polymer was added with mixing. Once uniform, this mixture was poured onto aluminum foil, allowed to cool to room temperature, removed from the aluminum foil and broken into suitably sized pieces. This formula made too soft a flake and Example 9 was made to correct that by removing the Glyceryl Tricaprate/caprylate and increasing the cationic surfactant and the cetearyl alcohol. Example 9 was made by combining the first three ingredients then heating with mixing to melt and solubilize them. Once uniform, the mixture was cooled to 65 to 75° C. and the polymer was added with mixing. Once uniform, this mixture was poured onto aluminum foil, allowed to cool to room temperature, removed from the aluminum foil and broken into suitably sized pieces. This resulted in a flake that was not uniform because the Polyquaternium 37 formed lumps when mixed with the high and low HLB surfactants. Switching to Guarhydroxypropyltrimonium chloride (Example 10) resolved the lumping problem. Example 10 was made by combining the first three ingredients then heating with mixing to melt and solubilize them. Once uniform, the mixture was cooled to 65 to 75° C. and the polymer was added with mixing. Once uniform, this mixture was poured onto aluminum foil, allowed to cool to room temperature, removed from the aluminum foil and broken into suitably sized pieces. Example 10 produced Test Lotion Formulas that showed signs of instability. Increasing the Behentrimonium chloride and using both Polyquaternium 37 and Guarhydroxypropyltrimonium Chloride gave Example 11—which was made by combining the first three ingredients then heating with mixing to melt and solubilize them. Once uniform, the mixture was cooled to 65 to 75° C. and the (combined) polymers were added with mixing. Once uniform, this mixture was poured onto aluminum foil, allowed to cool to room temperature, removed from the aluminum foil and broken into suitably sized pieces. The Test Lotion Formula for Example 11 produced stable emulsions.

Example 12 was made to reduce the amount of high HLB surfactant and to increase the viscosity of the Test Lotion Formula. Example 12 was made by combining the first four ingredients then heating with mixing to melt and solubilize them. Once uniform, the mixture was cooled to 65 to 75° C. and the polymers were added with mixing. Once uniform, this mixture was poured onto aluminum foil, allowed to cool to room temperature, removed from the aluminum foil and broken into suitably sized pieces. The Test Lotion Formula DID NOT produce stable emulsions—showing separation at 50° C. after one week and the viscosity was significantly lower than that of Example 11.

The Test Emulsions were evaluated for pH, viscosity and tested for stability at RT, 50° C. and Freeze/Thaw. Photomicrographs of the emulsions were taken.

Example 13 discloses the use of Chitosan Citrate as a hydrophilic emulsion stabilizing polymer. The process for making Chitosan Citrate Powder starts with dissolving 5 grams of Chitosan Powder in 90 grams of water with 5 grams of citric acid. When uniform and clear, this mixture is dried for 24 hrs in a 65° C. oven. The brittle solid is then pulverized and classified with a 300 micron screen. The resulting powder is used to make Example 13. The first 3 ingredients are mixed and heated to 90 to 100° C. to completely dissolve all material. Once uniform, the mixture is cooled to 65 to 75° C. and the chitosan citrate powder is added with mixing. Once the mixture is uniform and the polymer powder is evenly dispersed, it is poured onto aluminum foil, allowed to cool to room temperature, removed from the aluminum foil and broken into suitably sized pieces. The test lotion made from Example 13 is stable for 4 weeks at 50° C.

Figure 4:
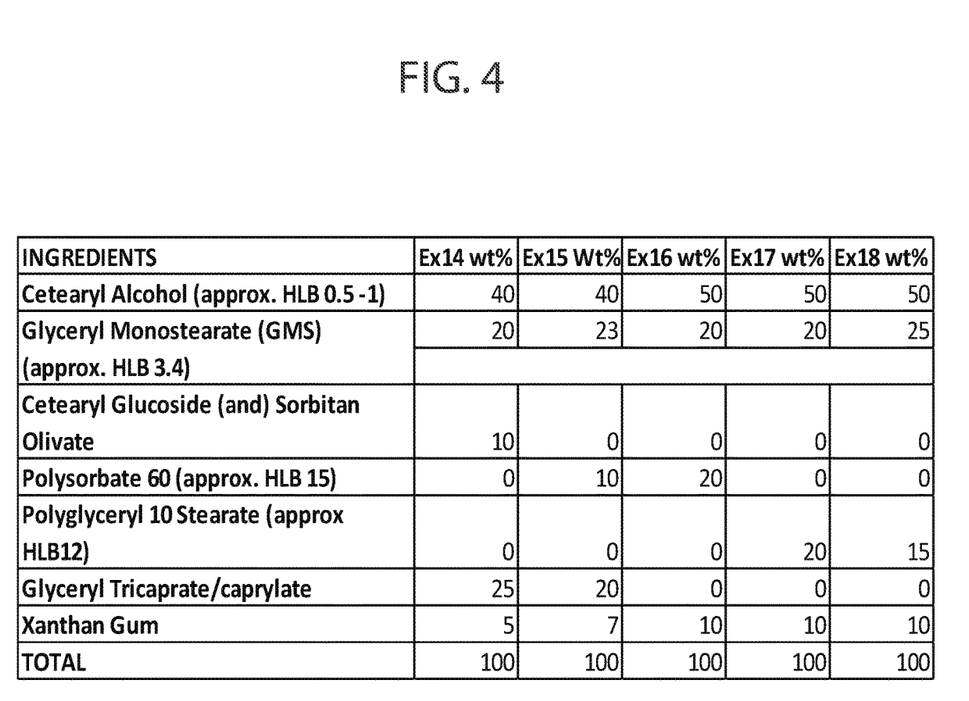
FIG. 4 is a listing of ingredients in wt % for examples 14-18.

FIG. 4 shows the ingredients in wt % for examples 14-18 which are for nonionic cosmetic emulsion bases.

These examples illustrate the concept of combining the high and low HLB surfactants and a stabilizing polymer to form a single composition using nonionic high HLB surfactants. Nonionic Emulsion Bases can be made with cationic, anionic and nonionic water soluble polymers or combinations. However, combinations of anionic and cationic water soluble polymers will generally be incompatible. Note that if anionic or cationic polymers are used, the resulting emulsion blend will not be nonionic.

The Examples 14 and 15 were made by combining the first four ingredients then heating with mixing to melt and solubilize them. Once uniform, the mixture was cooled to 65 to 75° C. and the polymer was added with mixing. Once uniform, the mixture was poured onto aluminum foil, allowed to cool to room temperature, removed from the aluminum foil and broken into suitably sized pieces. This formula made too soft a flake and the further Examples were made without the Glyceryl Tricaprate/caprylate and with increased cetearyl alcohol. The first attempt with Polysorbate 60 (Example 16) was made by combining the first three ingredients then heating with mixing to melt and solubilize them. Once uniform, the mixture was cooled to 65 to 75° C. and the polymer was added with mixing. Once uniform, the mixture was poured onto aluminum foil, allowed to cool to room temperature, removed from the aluminum foil and broken into suitably sized pieces. Example 16 did not make stable emulsions when used in the Test Lotion Formula (Example 1) without Triethanolamine. The last two Examples (17 and 18) were made by combining the first three ingredients then heating with mixing to melt and solubilize them. Once uniform, the mixture was cooled to 65 to 75° C. and the polymer was added with mixing. Once uniform, the mixture was poured onto aluminum foil, allowed to cool to room temperature, removed from the aluminum foil and broken into suitably sized pieces. The change to Polyglyceryl-10 Stearate (Example 17) produced better stability results with the Test Lotion Formula (Example 1), but ultimately, it was found that reducing the Polyglyceryl-10 Stearate to 15% (Example 18) gave improved stability when used in the Test Lotion Formula.

The Test Emulsions were evaluated for pH, viscosity and tested for stability at RT, 50° C. and Freeze/Thaw. Photomicrographs of the emulsions were taken.

Accordingly, while several embodiments of the present invention have been shown and described, it is to be understood that many changes and modifications may be made thereunto without departing from the spirit and scope of the invention as defined in the appended claims.

I claim:

1. A method for making cosmetic emulsions comprising the steps of:
   providing at least one fatty alcohol;
   providing at least one low HLB surfactant;
   providing at least one high HLB surfactant;
   mixing said at least one fatty alcohol with said at least one low HLB surfactant and said at least one high HLB surfactant together to form a substantially uniformly dispersed mixture;
   heating the mixture to between 65 and 75 degrees Celsius;
   adding at least one water soluble polymer to the uniformly dispersed mixture to form an emulsifier blend, now containing the uniformly dispersed water soluble polymer;
   adding the emulsifier blend to a cosmetic emulsion oil phase to ensure greater dispersion of the water soluble polymer; and
   adding the emulsifier blend in the oil phase to the water phase.

2. The method of claim 1, wherein the oil phase of said cosmetic emulsion comprises at least one of: preservatives, medicaments, sunscreens, extracts, fragrances, colorants, pigments, clays, waxes, or polymers.

3. The method as in claim 2, wherein the water phase of said cosmetic emulsion comprises at least one of: preservatives, medicaments, sunscreens, extracts, fragrances, colorants, pigments, clays, polymers, humectants, moisturizers, proteins.

4. The process for creating an emulsifier as in claim 1, wherein the step of adding the water phase comprises adding a 50% heated water phase.

5. The process as in claim 4, further comprising the step of adding the water phase comprises adding a remaining water phase in a cold form.

6. The method of claim 1 In which the fatty alcohol is cetyl alcohol, stearyl alcohol or a mixture of the two.

7. The method of claim 1 in which the low HLB surfactant is glyceryl monostearate.

8. The method of claim 1 in which the high HLB surfactant is anionic.

9. The method of claim 1 in which the high HLB surfactant is cationic.

10. The method of claim 1 in which the high HLB surfactant is nonionic.

11. The method as in claim 8, wherein the high HLB surfactant is anionic and comprises fatty acid soaps comprising any one of stearic acid soaps from alkali metal or ammonium ion salts; Behenic acid soaps from alkali metal or ammonium ion salts; Palm itic acid soaps from alkali metal or ammonium ion salts and combinations of the above surfactants.

12. The method as in claim 9, wherein the high HLB surfactant is cationic and comprises any one of:
Behenyltrimethylammonium chloride (INCI Behentrimonium Chloride)
Behenyltrimethylammonium methosulfate (INCI Behentrimonium Methosulfate)
Distearyldimethylammonium Chloride (INCI Quaternium 18) and combinations of the above surfactants.

13. The method as in claim 10, wherein the high HLB surfactant is nonionic and comprises any one of:
Polysorbate 60, Cetearyl Glucoside, Polyglyceryl 10 Stearate and combinations of the above surfactants.

* * * * *

UNITED STATES PATENT AND TRADEMARK OFFICE
CERTIFICATE OF CORRECTION

| | |
|---|---|
| PATENT NO. | : 11,839,669 B2 |
| APPLICATION NO. | : 17/696494 |
| DATED | : December 12, 2023 |
| INVENTOR(S) | : John Clyde Carson |

It is certified that error appears in the above-identified patent and that said Letters Patent is hereby corrected as shown below:

In the Claims

In Column 8, Line 52 (Line 1 of Claim 4), please change:
"The process for creating an emulsifier as in claim 1,..."
To correctly read:
-- The method as in claim 1,... --

In Column 8, Line 55 (Line 1 of Claim 5), please change:
"The process as in claim 4,..."
To correctly read:
-- The method as in claim 4,... --

Signed and Sealed this
Twenty-third Day of April, 2024

Katherine Kelly Vidal
*Director of the United States Patent and Trademark Office*